US00PP11317P

United States Patent [19]

Heims

[11] Patent Number: Plant 11,317

[45] Date of Patent: Mar. 28, 2000

[54] *OMPHALODES CAPPADOCICA* PLANT NAMED 'LILAC MIST'

[75] Inventor: Dan M. Heims, Portland, Oreg.

[73] Assignee: Terra Nova Nurseries, Inc., Portland, Oreg.

[21] Appl. No.: 09/060,058

[22] Filed: Apr. 14, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Wendy A Baker
*Attorney, Agent, or Firm*—Klarquist Sparkman Campbell Leigh & Whinston, LLP

[57] ABSTRACT

A new and distinct form of Omphalodes characterized by unique flower color.

1 Drawing Sheet

The present invention relates to a new and distinct sport of Omphalodes which originated as a tissue culture mutation of *Omphalodes cappadocica* 'Starry Eyes' (unpatented).

The new Omphalodes is a result of a tissue culture sport at Terra Nova Nurseries, Inc., in Canby, Oreg. This sport was selected from a large group of clonally propagated plants. *Omphalodes cappadocica* 'Starry Eyes' plants were retained to observe habit and to compare with the new variety. The new variety has been reproduced only by asexual propagation (tissue culture). Each of the progeny exhibits identical characteristics to the original plant and is unlike any Omphalodes offered by any American nursery or book as evidenced by the following characteristic: Unique flower color. Asexual propagation by tissue-culture as done in Tigard, Oreg., shows that the foregoing characteristics and distinctions come true to form and are established and transmitted through succeeding propagations. Omphalodes is in the family Boraginaceae.

BRIEF DESCRIPTION OF THE PHOTOGRAPHS

The drawing shows plant in full bloom in April in Orgeon. The drawing depicts the plant as true to type as is photographically possible.

DETAILED PLANT DESCRIPTION

The following is a detailed description of the new Omphalodes based on observations of specimens in Canby, Oreg. The color descriptions are all based on The Royal Horticultural Society Colour Chart and the American Rhododendron Society publication: *A CONTRIBUTION TOWARD STANDARDIZATION OF COLOR NAMES IN HORTICULTURE.*

Foliage:
- *Type.*—Herbaceous.
- *Shape.*—Ovate to cordate.
- *Length.*—7.5–8.7 cm.
- *Width.*—5 cm.
- *Petiole length.*—7.5–8.5 cm.
- *Margins.*—Entire, ciliate.
- *Apex.*—Acute-acuminate.
- *Base.*—Obtuse.
- *Texture.*—Finely pilose.

- *Petiole texture.*—Sericeous.
- *Leaf arrangement.*—Basal clump.
- *Venation.*—Camptodromus, lateral veins prominent.

Size:
- *Height.*—20 cm (2 yr-old plant in Oregon).
- *Width.*—40 cm (2 yr-old plant in Oregon).

Flower:
- *Petal count.*—5 petals.
- *Petal shape.*—Rounded.
- *Flower type.*—Complete, rotate (wheel-shaped); calyx 5-parted.
- *Flower size.*—0.9 cm (from petal tip to petal tip).
- *Flower number.*—10–15 per panicle.
- *Height of plant in bloom.*—21 cm.
- *Blooming habit.*—Paniculate.
- *Bloom period.*—In Oregon, early March to late April, some rebloom in fall.

Color Characteristics

Foliage:
- *Mature leaves upper surface.*—Spring: R.H.S.143B Yellow Green Group (Strong Yellow Green ARS).
- *Mature leaves upper surface, summer through winter.*—R.H.S. 146A Yellow Green Group (Moderate Olive Green ARS).
- *Mature leaves lower surface.*—R.H.S. 147C Yellow Green Group (Moderate Yellow Green ARS).

Flowers: R.H.S. 85B Violet Group (Light Purple ARS) fading to R.H.S. 85D Violet Group.

DESCRIPTION OF ORIGINAL PLANT

*Omphalodes cappadocica* 'Starry Eyes' is identical in all aspects except for the flower color. *Omphalodes cappadocica* 'Starry Eyes' has white to pink centered blooms with a brilliant blue edge whereas *Omphalodes cappadocica* 'Lilac Mist' has even lilac coloring throughout the flower.

I claim:

1. A new and distinct hybrid of Omphalodes plant substantially as shown and described, characterized by its unique flower color.

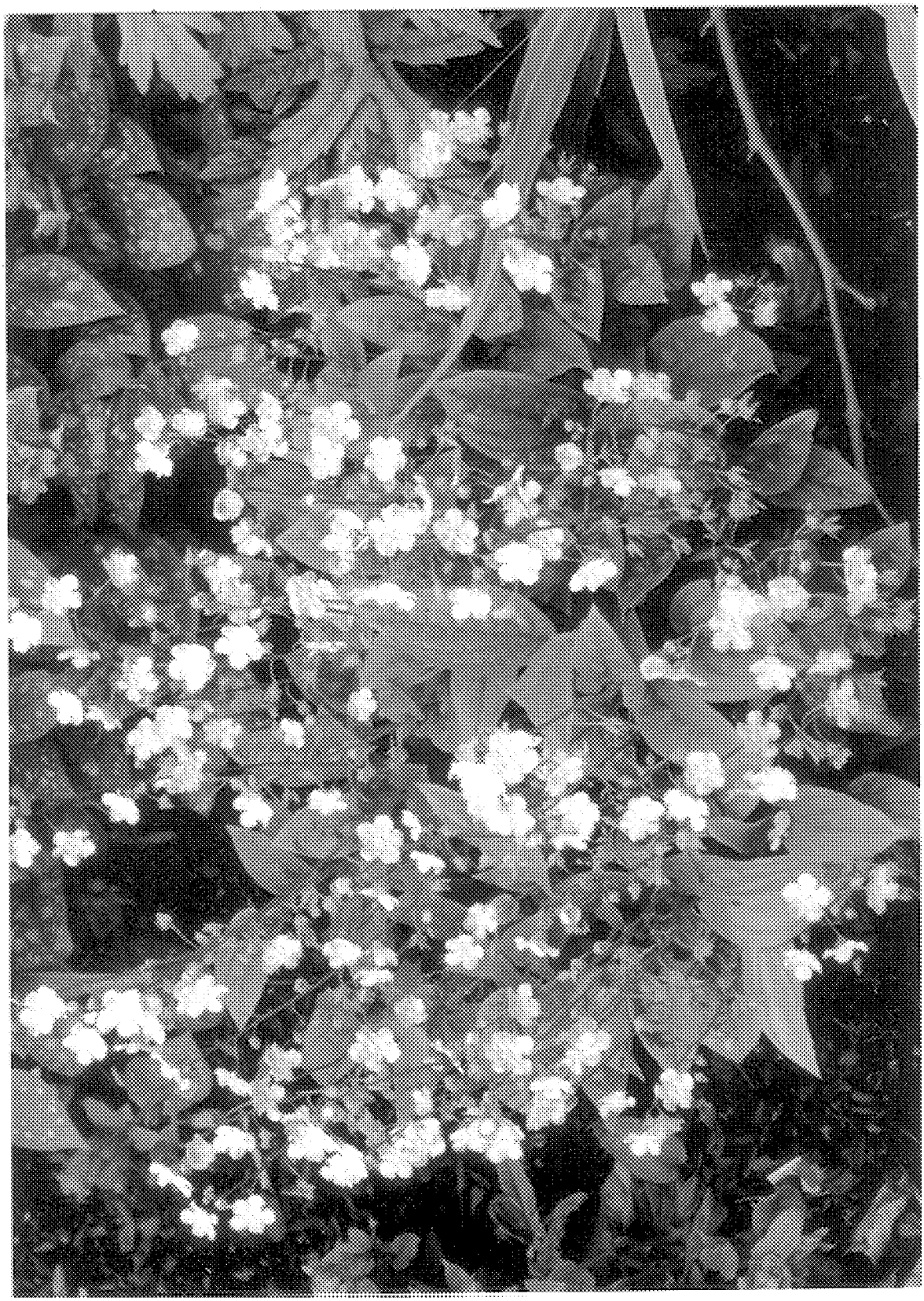

* * * * *